United States Patent
Konofal (10) Patent No.: US 9,637,447 B2
(45) Date of Patent: May 2, 2017

(54) LAUFLUMIDE AND THE ENANTIOMERS THEREOF, METHOD FOR PREPARING SAME AND THERAPEUTIC USES THEREOF

(75) Inventor: Eric Konofal, Senlis (FR)

(73) Assignee: NLS Pharma AG, Stans (CH)

( * ) Notice: Subject to any disclaimer, the term of this patent is extended or adjusted under 35 U.S.C. 154(b) by 0 days.

(21) Appl. No.: 13/980,708

(22) PCT Filed: Jan. 20, 2012

(86) PCT No.: PCT/EP2012/050881
§ 371 (c)(1),
(2), (4) Date: Jul. 19, 2013

(87) PCT Pub. No.: WO2012/098235
PCT Pub. Date: Jul. 26, 2012

(65) Prior Publication Data
US 2013/0295196 A1    Nov. 7, 2013

(30) Foreign Application Priority Data
Jan. 20, 2011   (FR) ..................... 11 50455

(51) Int. Cl.
| | | |
|---|---|---|
| *C07C 317/28* | (2006.01) | |
| *C07C 315/02* | (2006.01) | |
| *C07C 317/44* | (2006.01) | |
| *A61K 31/165* | (2006.01) | |
| *A61K 45/06* | (2006.01) | |

(52) U.S. Cl.
CPC .......... *C07C 317/28* (2013.01); *A61K 31/165* (2013.01); *A61K 45/06* (2013.01); *C07C 315/02* (2013.01); *C07C 317/44* (2013.01)

(58) Field of Classification Search
CPC ... C07C 315/02; C07C 317/44; C07C 317/28; A61K 31/165
See application file for complete search history.

(56) References Cited

U.S. PATENT DOCUMENTS

| | | | |
|---|---|---|---|
| 4,489,095 A | 12/1984 | Lafon | |
| 4,927,855 A * | 5/1990 | Lafon ................ | A61K 31/165 514/618 |

FOREIGN PATENT DOCUMENTS

| | | | | |
|---|---|---|---|---|
| CA | 1199916 | 1/1986 | | |
| EP | 0097071 | 12/1983 | | |
| FR | WO 2005028428 A1 * | 3/2005 | ........... | C07C 315/02 |
| WO | 01/12170 | 2/2001 | | |
| WO | 2005028428 | 3/2005 | | |
| WO | WO 2005028428 A1 * | 3/2005 | | |

OTHER PUBLICATIONS

Cao, J.; Prisinzano, T.E.; Okunola, O.M.; Kopajtic, T.; Shook, M.; Katz, J.L.; Newman, S.H. "SARs at the Monoamine Transporters for a Novel Series of Modafinil Analogues" ACS Med. Chem. Lett. 2011, 2, 48-52.*

Cao, J.; Prisinzano, T.E.; Okunola, O.M.; Kopajtic, T.; Shook, M.; Katz, J.L.; Newman, A.H. "SARs at the Monoamine Transporters for a Novel Series of Modafinil Analogues" ACS Med Chem Lett 2011, 2, 48-52 (available online Oct. 18, 2010).*

Biederman, J. et al., "Modafinil as therapy for ADHD in children: A 4-week, double-blind, placebo-controlled study," European Neuropsychopharmacology, (2004) vol. 14, Supplement 3:S364.

Billiard, M. et al, "EFNS guidlines of managemnts of narcolepsy," Eur J Neural, (2006) 13(10):1035-48.

Cao et al., "Structure-Activity Relationships at the Monoamine Transporters for a Novel Series of Modafinil (2-[(diphenylmethyl]sulfinyliacetamide) Analogues," ACS Med Chem Lett (2010) 2(1):48-52.

Chervin et al., "Associations between symptoms of inattention, hyperactivity, restless legs, and periodic leg movements," Sleep (2002) 15;25(2):213-218.

Golan, N. et al., "Sleep disorders and daytime sleepiness in children with attention-deficit/hyperactivity disorder," Sleep, (2002), 15(27):261-266.

Greenhill, L. et al., "Practice parameter for the use of stimulant medications in the treatment of children, adolescents, and adults," J Am Acad Child Adolesc Psychiatry, (2002) 41(2 Suppl):26S-49S.

Greenhill, L. et al., "A double-blind placebo-controlled study of modified-release methylphenidate in children with attention-deficit/hyperactivity disorder", Pediatrics. (2002), 109(3):E39.

Gruber, R. et al., "Instability of sleep patterns in children with attention-deficit/hyperactivity disorder," J Am Acad Child Adolesc Psychiatry, (2000), 39(4):495-501.

Lecendreux, M. et al., "M-C-Sleep and alertness in children with ADHD," J Child Psychol Psychiatry, (2000), 41 (6):803-812.

Palm, L. et al., "Sleep and wakefulness in preadolescent children with deficits in attention, motor control and perception," Acta Paediatr, (1992) 81:618-624.

Popper, C, "Pharmacologic alternatives to psychostimulants for the treatment of attention-deficit/hyperactivity disorder," Child Adolesc Psychiatr Clin N Am, (2000), 9(3):605-46, viii.

(Continued)

Primary Examiner — Brian-Yong Kwon
Assistant Examiner — Andrew S Rosenthal
(74) Attorney, Agent, or Firm — Pepper Hamilton LLP (57) ABSTRACT

The invention relates to the molecule having formula (I), as well as the enantiomers thereof, and to the use of same in the treatment of ADHD, narcolepsy or idiopathic hypersomnia.

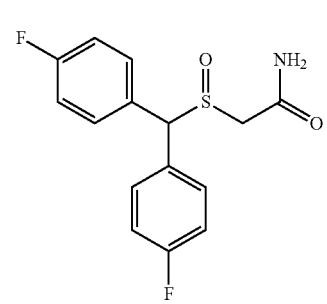

(I)

11 Claims, 2 Drawing Sheets

(56) References Cited

OTHER PUBLICATIONS

Robinson, D. et al., "Sodium oxybate: a review of its use in the management of narcolepsy," CNS Drugs, (2007) 21 (4):337-354, Erratum in CNS Drugs. 2007:21(8):692.
Spencer et al., "Adults with attention-deficit/hyperactivity disorder: a controversial diagnosis," J. Clin. Psychiatry, (1998) suppl. 7:59-68.
Weinberg A. et al., "Primary disoder of vigilance: a novel explanation of inattentiveness, daydeaming, boredom, restlessness, and sleepiness.," J Pediatr, (1992), 116:720-725.
Weiss, M. et al., "Adults with attention-deficit! hyper activity disorder: current concepts," J Psychiatr Pract. (2002) 28:99-111.

* cited by examiner

LAUFLUMIDE AND THE ENANTIOMERS THEREOF, METHOD FOR PREPARING SAME AND THERAPEUTIC USES THEREOF

The invention relates to the field of drugs useful in the treatment of disorders associated with a deficit of attention, of the regulation of attention and/or of wakefulness, in particular of attention-deficit/hyperactivity disorder (ADHD).

Attention-deficit/hyperactivity disorder (ADHD), which combines inattention, impulsivity and behavioral hyperactivity, is a common reason for child psychopathology consultations. According to studies, its prevalence in the general population of children is from 2% to 5%. The diagnosis is based on the clinical criteria defined in the Diagnostic and Statistical Manual of Mental Disorders (DSM-IV). Above all, ADHD is the exaggerated, permanent and continuous expression of behavioral symptoms not due to an educational, pedagogical or socioeconomic deficiency. The signs of inattention can persist beyond childhood and cause social, relational and affective difficulties.

The hypothesis according to which hyperactivity may be secondary to a disorder of the maintenance of wakefulness or a primary disorder of vigilance has been well documented over the past 20 years and has been expanded by several studies showing the involvement of the maintenance of attention in the origin of the disorder. In particular, Palm (1992), Lecendreux, Konofal et al. (2000) and Golan et al. (2004) have shown that children with ADHD suffer daytime sleepiness that is sometimes severe (low average value to multiple sleep latency tests), and showed that in certain cases they fell asleep more quickly or more frequently than the children in the control group when conditions favorable to sleep were proposed (the child lying down and calm under optimal noise and lighting conditions). The results of these studies undertaken to investigate dysfunction of wakefulness mechanisms in children with ADHD, supporting the hypothesis according to which daytime sleepiness may underlie behavioral symptoms, highlighted certain clinical aspects of this pathology that support the argument for the advantage of using eugregoric, awakening molecules in the symptomatological treatment of ADHD.

The stimulant substances used in the pharmacological treatment of ADHD, in particular in children, belong to several pharmacological classes: psychostimulants (amphetamine, methylphenidate, bupropion), eugregorics (modafinil, adrafinil), and monoamine oxidase B inhibitors (selegiline).

The most used and best known are as follows:
methylphenidate (MPH) is the reference treatment for ADHD in children, adolescents and adults. It is above all a psychostimulant known for its stimulating properties. Apart from its stimulating dopaminergic action on noradrenalin and dopamine release, via inhibition and reuptake, MPH has no effect on postsynaptic alpha-1 noradrenergic receptors (modification of sensitivity).
amphetamine (D,L-amphetamine) acts on the extra-vesicular release of noradrenalin and dopamine and therefore inhibits any form of storage. Because of its potential misuse and undesirable side effects its use remains either strictly limited or prohibited in most European nations.
modafinil ((±)-2(benzhydrylsulfinyl)acetamide) is an analeptic drug (Modiodal®) approved by the Food and Drug Administration (FDA) for the treatment of narcolepsy and of residual excessive daytime sleepiness associated with obstructive sleep apnea syndrome.

The EMA (formerly EMEA) has recommended it only for narcolepsy.

Modafinil was shown effective in the treatment of ADHD (WO01/12170) but was rejected by the FDA for cases of Stevens-Johnson syndrome.

Modafinil is the primary metabolite of adrafinil (2-((diphenylmethyl)sulfinyl)-N-hydroxyacetamide) (Olmifon®, Cephalon) and requires a higher dose to produce the same effects. It is a stimulant (eugregoric) whose complex mechanism of action is poorly understood. It does not cause dependency.

atomoxetine, a selective noradrenalin reuptake inhibitor and dopaminergic stimulant (by inhibition of reuptake in the prefrontal cortex), has shown effectiveness and good tolerance in ADHD in children and adults (Spencer at al., 1998; Popper 2000; Biederman et al., 2002).
It was approved by the FDA in November, 2002.
others: bupropion, caffeine, selegiline, etc.

Bupropion, a catecholamine reuptake inhibitor and antidepressant, is also a potential competitor in the treatment of ADHD.

Selegiline, a monoamine oxidase reuptake inhibitor, also has pharmacological properties similar to those of amphetamines. Its stimulatory action in the treatment of ADHD is known and its advantage in this use is possible.

Thus, the improvement in motor hyperactivity by dopaminergic psychostimulants is often very significant, but nevertheless insufficient.

This is because the stimulant substances used or which could be used to treat ADHD, in particular psychostimulants such as methylphenidate or amphetamines, often have a short plasma half-life, which leads to the appearance of on-off effects, i.e., an off effect accompanied by a rebound effect after a few hours, which are responsible for an aggravation of symptoms in the latter part of the night and disturb the ability to fall asleep.

Furthermore, some of these substances are metabolized in the body and, consequently, may be toxic to the patient.

Furthermore, certain particular symptoms such as insomnia, difficulties in falling asleep, getting up during the night, possibly due to excessive nighttime motor agitation, as well as additional disorders such as inattention, impatience and impulsivity, seem to resist any form of treatment [Chervin et al., Sleep 2002 15; 25(2):213-8; Gruber et al., J Am Acad Child Adolesc Psychiatry. 2000; 39(4):495-501].

Narcolepsy, first described by Jean-Baptiste-Édouard Gélineau, is a serious neurological disorder characterized by two main symptoms, narcolepsy and cataplexy. The principal symptom is the daily presence of irrepressible episodes of sleep. Cataplexy appears in about 3 cases out of 4. The sleep architecture is always disturbed. To suffer from narcolepsy is to pass directly from the waking state to paradoxical sleep with no intermediate stage.

Other secondary symptoms can appear, such as hypnagogic or hypnopompic hallucinations, sleep paralyses or automatic acts. It belongs to the dyssomnias, or sleep disorders.

Narcolepsy can be diagnosed by EEG.

The prevalence of narcolepsy in France is estimated at between 2 and 3 per 10,000 inhabitants.

Cataplexy, which is an abrupt loss of muscle tone with no change in consciousness, is a symptom not always present in narcoleptics. The prevalence of cataplexy ranges between 75% and 80% of narcoleptics.

Narcolepsy affects slightly more men than women. The appearance of the pathology has two main peaks, one during adolescence and one at about 40 years of age.

The principal characteristic of narcolepsy is daytime hypersomnolence, due to irrepressible bouts of sleep occurring several times per day and lasting a few seconds to 30 minutes, sometimes more, and sometimes in situations that can be delicate.(waiting in line in a store, travel by train or other public transport, business activities, etc.) or even dangerous (crossing the street, driving an automobile or motorcycle, using tools at home or work, bathing an infant, etc.).

These continuous and significant fluctuations in vigilance are accompanied by attention difficulties and occasionally temporary memory problems. They can lead to automatic reflexes (nonsense speech, arranging objects in unusual places, constantly losing keys or wallet, driving in an unexpected area, daydreaming that is unexpected—and sometimes compromising, etc.). Generally the bout of sleep is refreshing for an hour or two, and then a new bout of sleep follows. A narcoleptic's day is thus punctuated with alternating waking states and bouts of sleep.

Hypersomnolence and bouts of cataplexy can be highly disabling and can limit or exclude professional activities as well as many other types of activity. The ill can at times suffer increasing social isolation. It is not rare for narcolepsy to be a cause of subsequent depression.

Existing treatments target only symptom relief and not the cause.

Current treatments for the symptom of hypersomnolence consist of awakening molecules such as modafinil or stimulating molecules such as methylphenidate, amphetamine salts or methamphetamine.

Against the symptom of cataplexy, the use of sodium oxybate (sodium gamma-hydroxybutyrate), which enables a certain form of restoration of deep slow-wave sleep when taken at bedtime and during the night, is the reference treatment today. (Robinson D M, Keating G M. CNS Drugs. 2007; 21(4):337-54. Review. Erratum in: CNS Drugs. 2007; 21(8):692.)

Other molecules can also be used. These are molecules having an inhibitory role in the reuptake of noradrenalin and/or serotonin and/or dopamine, and thus drugs further known for their antidepressant role (clomipramine, imipramine, protriptyline, venlafaxine).

Idiopathic hypersomnia is a very rare disease characterized by excessive daytime sleepiness of unknown origin.

The symptoms generally begin in young adulthood, before the age of 30. The frequency of the disease, although difficult to estimate due to its rarity, affects 1 in 10,000 to 500,000 inhabitants (5 to 10 times rarer than narcolepsy).

No cause has been found for this hypersomnia, which is why it is described as idiopathic.

It is a virtually permanent excessive daytime sleepiness that fluctuates very little during the day. This sleepiness forces the subject to take one or more naps, which can last: several hours, over the course of the day. A key element of the clinical diagnosis is that these naps do not have the refreshing nature that they have normally or in narcolepsy (the subject is always just as tired after the nap).

Their nighttime sleep is most often of very good quality, with very little awakening. On the other hand, awakening in the morning is particularly difficult (sleep intoxication) and there is an inertia upon awakening, i.e., the subject exhibits very slowed psychomotor functioning and even confusion.

Patients experience permanent fatigue, decreased mental performance, memory lapses and difficulty concentrating.

The difference with narcolepsy is that cataplexies are not present and sleep paralyses or hypnagogic hallucinations are only rarely present. Officially, the difference in diagnosis between hypersomnia and narcolepsy lies in the presence of cataplexy or of several episodes of falling into paradoxical sleep during a multiple sleep latency test (MSLT).

The MSLT shows sleepiness during the day which is not always abnormally rapid but which is always in the absence of paradoxical sleep (SOREM).

The treatment generally makes it possible for patients to lead a normal working life by eliminating the embarrassment of waking from bouts of daytime sleep. It is based, as for narcolepsy, on modafinil or amphetamine derivatives such as methylphenidate, but in case of failure other treatments such as Teronac® (mazindol) or Dexamine® (dextroamphetamine) can be tried. Stimulating antidepressants can be useful (Prozac®, Effexor®). Advice on how to achieve a good night's sleep, in particular the avoidance of naps, can also help relieve the disability created by this disease, but it remains sometimes ineffective.

There thus exists a real need to develop novel treatments for ADHD, narcolepsy and idiopathic hypersomnia that would provide better results than those obtained with current treatments based on psychostimulants, would treat symptoms resistant to current treatments with no symptom rebound effect, and would have a low toxicity.

Surprisingly and unexpectedly, the inventors have synthesized a molecule similar to modafinil and adrafinil and have shown that it is more effective than these two molecules in their indications with fewer side effects.

This molecule is lauflumide, or (2-((bis(4-fluorophenyl)methane)sulfinyl)acetamide:

This molecule has a chiral center at the sulfoxide (—S═O) group.

Consequently, the invention first relates to the lauflumide molecule in its racemic form or in its various enantiomeric forms:
- dextrorotatory enantiomer (dextro-lauflumide) or (+) enantiomer ((+)-lauflumide) or D enantiomer (D-lauflumide), and
- levorotatory enantiomer (levo-lauflumide) or (−) enantiomer ((−)-lauflumide) or L enantiomer (L-lauflumide).

The dextrorotatory enantiomer corresponds to the R enantiomer.

The levorotatory enantiomer corresponds to the S enantiomer.

According to the present invention, and when not specified otherwise, the term "lauflumide" refers to lauflumide in its racemic form or in its enantiomeric forms.

Advantageously, the invention relates to an optically pure lauflumide enantiomer in an enantiomeric excess of more than 95%, preferably of more than 96%, more preferably of more than 97%, even more preferably of more than 98%, particularly preferably of more than 99%. Preferably, this enantiomer is D-lauflumide or (+)-lauflumide or dextrolauflumide (dexlauflumide).

D-Lauflumide is more effective than the racemic mixture of lauflumide.

Lauflumide is not an amphetamine. Consequently, it does not have the side effects of amphetamines.

It is 20 times more effective than adrafinil and 4 times more effective than modafinil.

Lauflumide constitutes a therapeutic alternative to methylphenidate and amphetamine in ADHD and to modafinil in narcolepsy and idiopathic hypersomnia.

Lauflumide (racemic mixture) has an expected effectiveness in plasma of 6 to 7 hours. Only combinations of methylphenidates (immediate release and extended release) can successfully treat ADHD during the day. The same is true with amphetamine and modafinil. However, these combinations require perfect logistics (distributing and taking doses) and are a real limit to effectiveness over time. Lauflumide is thus a genuine alternative to the molecules approved to date for ADHD, narcolepsy and idiopathic hypersomnia.

The present invention is thus a real innovation on both the therapeutic level and the psychosocial level.

Another aspect of the invention relates to lauflumide, or (2-((bis(4-fluorophenyl)methane)sulfinyl)acetamide, as a drug.

According to the invention, the patient is selected from the group comprised of newborns, children, adolescents and adults.

According to an aspect of the invention, lauflumide is used as a drug according to a dosing schedule of 1 to 600 mg per day, preferably according to a dosing schedule of 50 to 400 mg per day.

Another aspect of the invention relates to lauflumide for use in the treatment of ADHD and/or associated or comorbid symptoms.

Another aspect of the invention relates to the use of lauflumide for the manufacture of a drug intended for the treatment of ADHD and/or associated or comorbid symptoms.

In the context of the invention, the diagnosis of ADHD is based on the clinical characteristics defined by the international classification, DSM-IV (Diagnostic and Statistical Manual of Mental Disorders, $4^{th}$ ed, 1994).

The DSM-IV criteria include three dimensions (inattention, impulsivity and hyperactivity), normal intellectual ability (IQ>80, for ages 5 to 12), iron deficiency but not anemia and thus normal hemoglobin level.

"Symptom of ADHD" refers to the primary symptoms of the DSM-IV, namely inattention, impulsivity and daytime and nighttime motor hyperactivity, and to secondary symptoms such as impatience, oppositional disorders, restless legs syndrome and insomnia.

Insomnia refers to:
a. difficulty falling asleep;
b. nighttime motor hyperactivity and awakening during the night, and
c. psychopathological insomnia, generally chronic and related to anxiety, stress and depression.

According to an aspect of the invention, lauflumide is used in the treatment of ADHD in combination with iron as a combination product for simultaneous, separate or sequential administration.

Preferentially, iron is used before the administration of lauflumide.

According to the present invention, the term "iron" refers to iron in the form of an iron atom, iron salt or organic iron, or any formulation containing pharmaceutically acceptable iron. Among pharmaceutically acceptable iron salts, mention may be made of ferrous salts and ferric salts, preferably ferric ammonium citrate, ferric pyrophosphate, ferrocholinate, ferrous ascorbate, ferrous aspartate, ferrous chloride, ferrous sulfate, ferrous tartrate, ferrous fumarate, ferrous gluconate, ferrous gluceptate, ferrous glycine sulfate, ferrous lactate, ferrous oxalate and ferrous succinate.

Alternatively, the pharmaceutically acceptable iron is in the form of iron dextran, iron sucrose, iron polymaltose or sorbitol.

According to an aspect of the invention, lauflumide is used in the treatment of ADHD in combination with at least one compound selected from psychostimulants as a combination product for simultaneous, separate or sequential administration.

Suitable psychostimulants are thus dopamine and/or noradrenalin reuptake inhibitors and catecholamine agonists. Among these, mention may be made, in a non-exhaustive manner, of:

1) Psychostimulants: methylphenidate, modafinil, atomoxetine and amphetamines such as d-amphetamine, dexedrine and dexamphetamine.
2) L-dopa: levodopa.
3) Selective dopamine agonists: pramipexole, ropinirole, lisuride, pergolide, cabergoline, etc.

When lauflumide is used in combination with iron, the dosing schedule for iron is 50 to 200 mg of iron element per day for 3 months (if ferritin is <30 µg/l).

When lauflumide is used in combination with a psychostimulant, the dosing schedule for the psychostimulant is 10-30 mg/day of methylphenidate, 100 to 400 mg/day of modafinil. Combination with an amphetamine salt is not advised.

Another aspect of the invention relates to a treatment method including the administration of an effective quantity of lauflumide to a patient suffering from ADHD, preferably in an amount of 1 to 400 mg per day, more preferably according to a dosing schedule of 200 to 300 mg per day.

Another aspect of the invention relates to lauflumide for use in the treatment of narcolepsy or idiopathic hypersomnia.

Another aspect of the invention relates to the use of lauflumide for the manufacture of a drug intended to treat narcolepsy or idiopathic hypersomnia.

Another aspect of the invention relates to a treatment method including the administration of an effective quantity of lauflumide to a patient suffering from narcolepsy or idiopathic hypersomnia, preferably in an amount of 1 to 400 mg per day, more preferably according to a dosing schedule of 200 to 300 mg per day.

According to an aspect of the invention, lauflumide is used in the treatment of narcolepsy or idiopathic hypersomnia in combination with at least one compound selected from serotoninergic antidepressants and sodium gamma-hydroxybutyrate as a combination product for simultaneous, separate or sequential administration.

This combined administration will be carried out under the same administration conditions and dosing schedules as those proposed with modafinil. (Billiard M. at al.; EFNS Task Force. Eur J Neurol. 2006; 13(10):1035-48 and Greenhill L L. et al.; American Academy of Child and Adolescent Psychiatry. J Am Acad Child Adolesc Psychiatry. 2002; 41(2 Suppl):26S-49S. Review.)

Another aspect of the invention relates to a pharmaceutical composition including lauflumide as an active ingredient and one or more pharmaceutically acceptable excipients.

The compounds or compositions according to the invention can be administered in various ways and in various forms well-known to the person skilled in the art. Thus, they can be administered by systemic, oral, anal or parenteral route, for example by intravenous, intramuscular, subcutaneous, transdermal or intraarterial route. Preferably, they are administered orally.

For injections, the compounds are generally provided as liquid suspensions. They can also be administered in the form of gels, oils, tablets, suppositories, powders, capsules, aerosols, etc., optionally by means of extended-release pharmaceutical forms or devices.

The pharmaceutical compositions of the invention can also include iron or one or more psychostimulants as active ingredients.

Another aspect of the invention relates to a pharmaceutical product including lauflumide and iron or one or more psychostimulants as active ingredients as a combination product for simultaneous, separate or sequential administration.

Another aspect of the invention relates to a method for preparing lauflumide including the following successive steps:

(i) preparation of Grignard reagent 2
(ii) preparation of fluorobenzhydrol 4 by condensation of Grignard reagent 2 with fluorobenzaldehyde 3 or ethyl formate 10
(iii) preparation of imidate 5 by adding thiourea to fluorobenzhydrol 4
(iv) saponification of imidate 5 and formation of sodium thiolate 6
(v) addition of chloroacetamide 7 and isolation of compound 8
(vi) oxidation of the sulfur of compound 8 into sulfoxide.

Preferentially, step (ii) occurs at −18° C.

Preferentially, step (iii) is carried out by adding thiourea to HBr.

Preferentially, step (iii) is carried out at 60° C. and precipitate 5 is obtained by heating to 80° C. and then cooling to room temperature.

Preferentially, precipitate 5 is filtered and washed between step (iii) and step (iv).

Preferentially, imidate 5 is saponified in step (iv) in aqueous solution by the addition of concentrated sodium hydroxide.

Preferentially, the oxidation in step (vi) of sulfur into sulfoxide is carried out with hydrogen peroxide in acetic acid.

Optionally, step (vi) is followed by a step (vii) of precipitation of lauflumide 9 after dilution in water of the reaction medium obtained after step (vi).

Optionally, step (vii) is followed by a step (viii) of crystallization of lauflumide 9, preferentially in a MeOH/H$_2$O mixture.

The following figures and examples illustrate the invention without limiting its scope.

Key: Before=session before the drug
Under=session under the drug
After=session after the drug

EXAMPLE 1

Synthesis of Lauflumide

Synthesis begins with the preparation of Grignard reagent 2 from aromatic bromide 1 with magnesium in ether. Fluorobenzaldehyde 3 is added at −18° C. to Grignard solution 2 to give fluorobenzhydrol 4. It should be noted that instead of using fluorobenzaldehyde 3, it is possible to use ethyl formate to condense 2 units of Grignard 2. This option is economically advantageous as fluorobenzaldehyde 3 is relatively expensive.

Fluorobenzhydrol 4 is added at 60° C. to a preformed aqueous solution of thiourea with HBr. After heating to 80° C., the solution is allowed to cool to room temperature and then precipitate 5 is filtered and washed with cold water. Precipitate 5 is then suspended in an aqueous solution and then freshly prepared concentrated soda is added to the mixture to saponify imidate 5. Sodium thiolate 6 is formed and after addition of chloroacetamide 7 compound 8 can be isolated.

The oxidation of sulfur into sulfoxide is carried out with hydrogen peroxide in acetic acid. After the reaction, the reaction medium is diluted in water and lauflumide 9 precipitates rather quickly. Lauflumide 9 is then recrystallized in a MeOH/H$_2$O mixture.

EXAMPLE 2

Effects of Lauflumide Compared with Mazindol and Modafinil in an ADHD Model

Principle

Impulsivity is a symptom of ADHD.

The test of waiting ability in a T-maze consists in offering a rat a choice between a quick and immediate food reward and a large but delayed reward. In adult Wistar rats, numerous antidepressants such as serotonin or noradrenalin reuptake inhibitors increase the number of choices for the large but delayed reward, indicating an improvement in waiting ability, i.e., a decrease in impulsivity [2,3].

Previous results have shown that methylphenidate increases the number of choices for the large but delayed reward in young Wistar rats, but not in adult Wistar rats, spontaneously hypertensive rats (SHR) and Wistar Kyoto (WKY) rats [4]. These results were confirmed by the discoveries that stimulating drugs (methylphenidate and amphetamine), non-stimulating noradrenalin reuptake inhibitors (atomoxetine and desipramine) and an alpha-2 adrenergic receptor agonist (clonidine) improved waiting ability in young rats subjected to the T-maze test [5,6]. Given that these drugs reduce the symptoms of ADHD, including impulsivity [7], these data indicate that the T-maze test with young animals is suitable for testing improvement in impulsivity control by drugs for the treatment of ADHD.

The goal of the present study is to examine whether lauflumide in the form of its racemic mixture or its D form ((+) enantiomer), administered in 3 doses before the test, improves waiting ability in young Wistar rats subjected to the T-maze test. An improvement in waiting ability by this compound would indicate that this compound reduces impulsivity and, consequently, could be useful in the treatment of ADHD. Methylphenidate and d-amphetamine are used as a reference product in the same experiment.

Materials and Methods

All of the experiments are carried out between 8:00 a.m. and 6:00 p.m. at room temperature (22±1.5° C.) under artificial lighting in a calm setting.

1. Animals

Male Wistar AF rats (Centre d'Elevage Rene Janvier, France) are used, aged 22 days at the beginning of the experiment and between 30 and 42 days at the time the molecules are administered.

Figure 1:
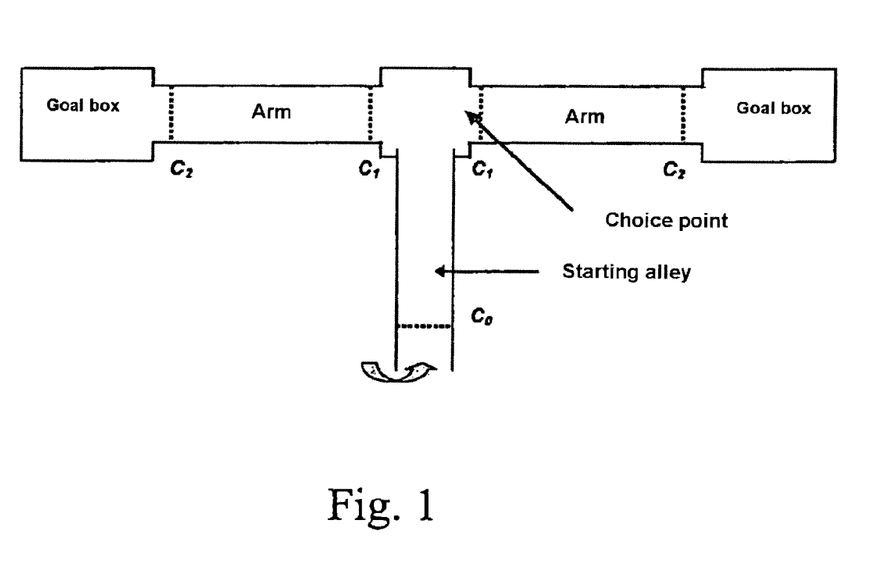
FIG. 1: Diagram of the T-maze test. c0, c1 and c2=location of guillotine doors.

Number of animals: 100 divided into 3 groups.
Temperature: 22±1.5° C.
Humidity: 50±25%.
Light: 50 lux; 7:00 a.m.-7:00 p.m.
Food: A04 (Safe, France); 5-10 g/day/animal.
Water available ad libitum 2. Molecules Tested Mazindol: 1, 3 and 10 mg/kg intraperitoneally
Methylphenidate: 3 mg/kg intraperitoneally
D-amphetamine: 1 mg/kg intraperitoneally
Modafinil: 64 and 128 mg/kg orally
Lauflumide: 64 and 128 mg/kg orally
D-Lauflumide: 64, 128 and 256 mg/kg orally
Placebo: 1 ml/kg intraperitoneally 3. Materials The experiments were carried out in two identical T-mazes (FIG. 1) made of opaque gray plastic tubes (inner diameter: 7.5 cm), consisting of a starting alley (30 cm long), a transparent plastic box, (10 cm wide, 10 cm deep and 10 cm high) and two arms (35 cm long) each leading to a rectangular black plastic box (18 cm wide, 30 cm deep, 10 cm high). The removable, gray plastic guillotine doors can be inserted in vertical slots located at the entrance to the starting alley and at the end of each arm. One of the goal boxes (left or right, depending on the rat) is continuously provided with a large reward, the other with a small reward. The large and small rewards consist of 5 and 1 pellets, respectively (20 mg, Technical & Scientific Equipment GMBH, Germany). The pellets are placed in a translucent cup before each test.

4. T-Maze Experimental Protocol

The T-maze test is a validated test which makes it possible, by extrapolation to man, to verify the effectiveness of pharmacological agents effective in ADHD.

Training Phase $1^{st}$ phase: habituation. The animals are first subjected to 2 to 6 habituation sessions of 5 minutes each. The rat is gently placed in the starting alley, which is then closed off by a guillotine door inserted in the slot (reference c0 in FIG. 1). The animal is allowed to freely explore the device and to eat the rewards placed in the cups.

$2^{nd}$ phase: pre-training. A door is placed in slot c2 near each goal box and then the rat is placed in the starting alley. When it enters one of the two arms, a door is inserted behind it in slot c1 near the choice point and the door placed in slot c2 is removed. Once the animal enters the goal box, the door is replaced in slot c2. The rat is removed from the goal box as soon as it eats the pellets. The animal is then returned to its cage for 2 to 3 minutes. One to three times per day, each rat is subjected to five test sessions. In four to 12 sessions, the rat chooses the arm leading to the large reward in more than 80% of the tests. The training phase then begins.

$3^{rd}$ phase: training. During training the rats 1 to 4 times/day undergo sessions of 5 tests during which a delay is introduced before access to the large reward is granted. After a door is placed in slot c2 near each goal box, the rat is placed in the starting alley. When it enters one of the two arms, a second door is inserted behind it in slot c1 near the choice point, so that the rat choosing the training arm with the large reward can be held in this arm for 30 seconds—the waiting period—before having access to the reinforcement. If not, if the animal chooses the arm leading to the small reward, the door placed in slot c2 is immediately removed, allowing the animal to enter the goal box. The testing of the drugs begins when the animal chooses the large reward delayed by 30 seconds in 2 tests in 5 (or fewer) during two consecutive sessions and in 1 test in 5 (or fewer) in the following session. Animals that do not meet this criterion within 12 sessions are eliminated from the experiment.

Test Phase

The test sessions are as follows:
two pre-drug sessions,
two sessions under the drug,
two post-drug control sessions.

Two pre-drug control sessions are carried out the same day, with intervals of 2 to 4 hours. The sessions under drugs 1 and 2 are carried out one and two days after the pre-drug control sessions, respectively. The two post-drug control sessions are carried out one day after the session under drug 2. Mazindol, methylphenidate, d-amphetamine or placebo is administered before each drug session.

The animals are divided randomly into 10 groups (n=10 animals per group) and receive a total of two IP administrations (before each drug session) as follows:
carrier group: mazindol carrier 60 min pre-test,
group Maz-1: mazindol (1 mg/kg) 60 min pre-test,
group Maz-3: mazindol (3 mg/kg) 60 min pre-test,
group Maz-10: mazindol (10 mg/kg) 60 min pre-test,
group Mph 3: methylphenidate (3 mg/kg) 30 min pre-test,
group Modaf-64: modafinil (64 mg/kg) 120 min pre-test,
group Modaf-128: modafinil (128 mg/kg) 120 min pre-test,
group Lauf 64: lauflumide (64 mg/kg) 120 min pre-test,
group Lauf 128: lauflumide (128 mg/kg) 120 min pre-test,
group D-A 1: d-amphetamine (1 mg/kg) 30 min pre-test
group D-Lauf 64: D-lauflumide (64 mg/kg) 120 min pre-test
group D-Lauf 128: D-lauflumide (128 mg/kg) 120 min pre-test
group D-Lauf 256: D-lauflumide (256 mg/kg) 120 min pre-test.

5. Data Analysis

For each animal, the percentage that the large but delayed reward is chosen is calculated.

6. Results

Figure 2:
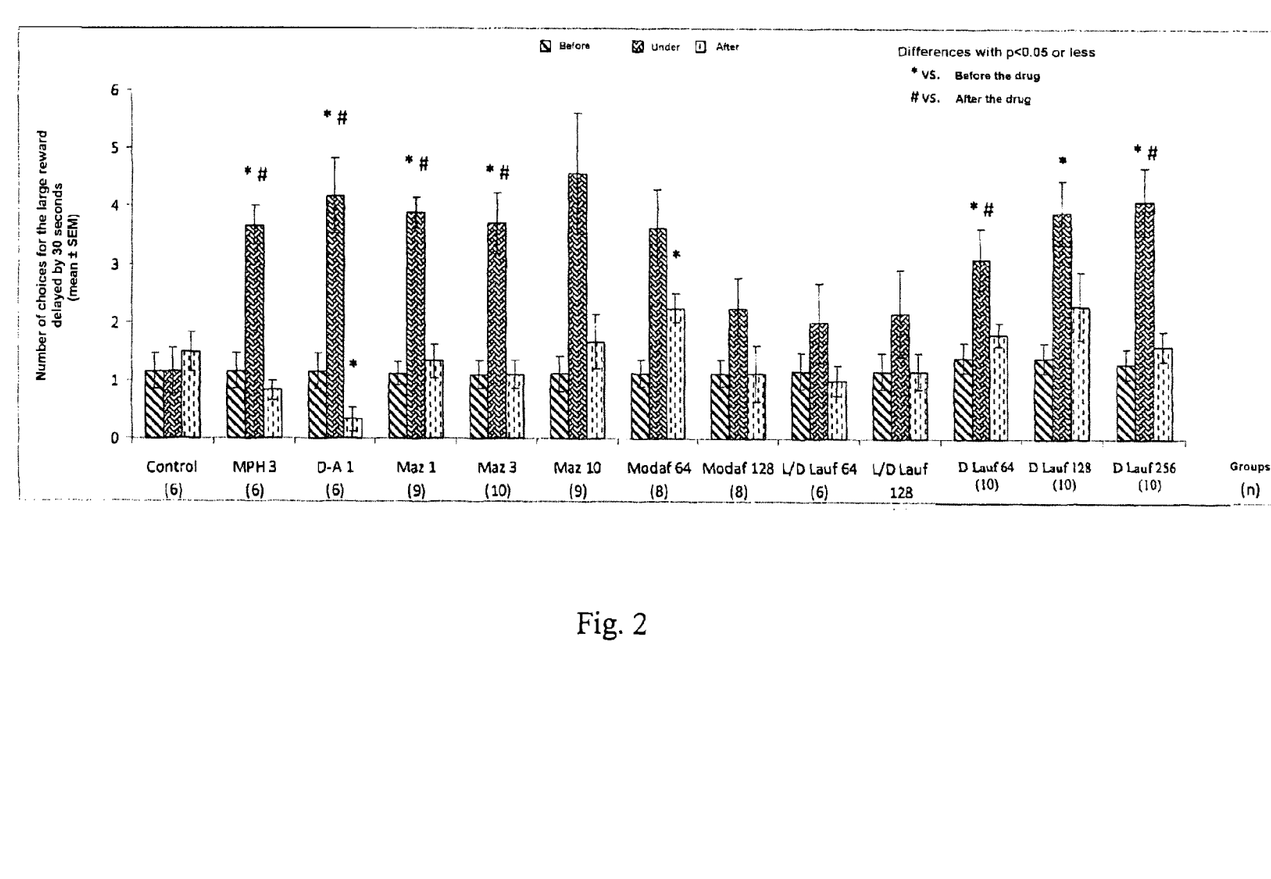
FIG. 2: Graphical representation of the T-maze test results (Example 2).

The results are compiled in FIG. 2.

Methylphenidate and d-amphetamine are used as reference products in the same experiment.

Mazindol, lauflumide in its racemic mixture form or its D form ((+) enantiomer), administered in 3 doses before the test, improve waiting ability in young Wistar rats subjected to the T-maze test compared to the control.

Mazindol and D-lauflumide are at least as effective as methylphenidate and d-amphetamine in improving waiting ability in young Wistar rats subjected to the T-maze test.

Mazindol and D-lauflumide are more effective than modafinil in improving waiting ability in young Wistar rats subjected to the T-maze test.

EXAMPLE 3

Preparation of D-Lauflumide ((+)-Lauflumide) or (R)-Lauflumide (S,S)-(−)-diethyl tartrate (1.14 ml, 6.62 mmol, 0.2 eq) is added to a solution of 2-(bis(4-fluorophenyl)methylthio) acetamide (9.7 g, 33.1 mmol, 1 eq) in dry toluene (100 ml) at 55° C., followed by Ti(OiPr)$_4$ (890 µl, 3.31 mmol, 0.1 eq) and water (30 µl, 1.66 mmol, 0.05 eq). After 50 minutes of stirring at 55° C., the reaction medium is cooled to room temperature and then diisopropylethylamine (590 µl, 3.31 mmol, 0.1 eq) is added followed by 80% cumene hydroperoxide (6.52 ml, 39.5 mmol, 1.2 eq). The reaction is stirred for 2 to 3 hours until the total conversion of the starting product into sulfoxide is achieved. The reaction is hydrolyzed by a 3% solution of citric acid in acetone (50 ml). After 20 minutes of stirring the reaction medium is filtered and then concentrated under vacuum. The residue is purified by silica column chromatography (50:50 AcOEt: petroleum ether and then 100% AcOEt). Recrystallization in a 50:50 methanol/water mixture followed by cooling at −18° C. makes it possible to obtain a crystallized fraction. The supernatant is concentrated and dried under vacuum to provide (R)-lauflumide in an enantiomeric excess of 94% (3.0 g, 29%).

REFERENCES

Billiard M, Bassetti C, Dauvilliers Y, Dolenc-Groselj L, Lammers G J, Mayer G, Pollmächer T, Reading P, Sonka K; EFNS Task Force. Eur J Neurol. 2006; 13(10):1035-48. *EFNS guidelines on management of narcolepsy.*

Chervin et al., *Associations between symptoms of inattention, hyperactivity, restless legs, and periodic leg movements.* Sleep 2002 15; 25(2):213-8

Golan N, Shahar E, Ravid S, Pillar G. *Sleep disorders and daytime sleepiness in children with attention-deficit/hyperactivity disorder.* Sleep. 15; 27:261-6; 2004

Greenhill L L, Pliszka S, Dulcan M K, Bernet W, Arnold V, Beitchman J, Benson R S, Bukstein O, Kinlan J, McClellan J, Rue D, Shaw J A, Stock S; American Academy of Child and Adolescent Psychiatry. J Am Acad Child Adolesc Psychiatry. 2002; 41(2 Suppl):26S-49S. Review. *Practice parameter for the use of stimulant medications in the treatment of children, adolescents, and adults.*

Gruber et al., *Instability of sleep patterns in children with attention-deficit/hyperactivity disorder.* J Am Acad Child Adolesc Psychiatry. 2000; 39(4):495-501

Lecendreux M, Konofal E, Bouvard M, Falissard B, Mouren-Simeoni M-C—*Sleep and alertness in children with ADHD.* J Child Psychol Psychiatry 41, 6, 803-12; 2000

Palm L, Persson E, Bjerre L, Elmqvist D—*Sleep and wakefulness in preadolescent children with deficits in attention, motor control and perception.* Acta Paediatr 81,618-24; 1992

Robinson D M, Keating G M. CNS Drugs. 2007; 21(4): 337-54. Review. Erratum in: CNS Drugs. 2007; 21(8):692. *Sodium oxybate: a review of its use in the management of narcolepsy.*

Weinberg A S, Brumback R A—*Primary disorder of vigilance: a novel explanation of inattentiveness, daydreaming, boredom, restlessness, and sleepiness.* J Pediatr 116, 720-5; 1992

Weis M, Murray C, Weiss G. *Adults with attention-deficit/ hyper activity disorder: current concepts.* J Psychiatr Pract. 28, 99-111; 2002

The invention claimed is:

1. A method of treatment of attention-deficit/hyperactivity disorder (ADHD) and/or associated or comorbid symptoms of ADHD comprising administering an effective amount of a compound of the following formula as the (R) enantiomer in an enantiomeric excess of more than 95% to a patient in need thereof.

2. The method according to claim 1 wherein the (R) enantiomer compound is in an enantiomeric excess of more than 99%.

3. The method according to claim 1 wherein the effective amount is from 1 to 400 mg.

4. The method according to claim 1 wherein from 1 to 400 mg of the (R) enantiomer compound is administered to the patient per day.

5. The method according to claim 1 wherein from 200 to 300 mg of the (R) enantiomer compound is administered to the patient per day.

6. The method according to claim 1 wherein the (R) enantiomer compound is administered to the patient orally.

7. The method according to claim 1 wherein the patient is a child.

8. The method according to claim 1 wherein the patient is also administered concomitantly, separately or sequentially, iron, one or more psychostimulants, one or more serotoninergic antidepressants, or sodium gamma-hydroxybutyrate.

9. The method according to claim 1 wherein the (R) enantiomer compound is in a pharmaceutical composition comprising one or more pharmaceutically acceptable excipients.

10. The method according to claim 9 wherein the pharmaceutical composition is a tablet.

11. The method according to claim 9 wherein the pharmaceutical composition further comprises iron, one or more psychostimulants, one or more serotoninergic antidepressants, or sodium gamma-hydroxybutyrate.

* * * * *